United States Patent [19]
King

[11] Patent Number: 6,013,047
[45] Date of Patent: *Jan. 11, 2000

[54] METHOD AND APPARATUS FOR PREVENTION OF FLUID INTRUSION IN A PROBE SHAFT

[75] Inventor: Robert W. King, Lexington, Mass.

[73] Assignee: Hewlett-Packard Company, Palo Alto, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/878,699

[22] Filed: Jun. 19, 1997

[51] Int. Cl.[7] .............................. A61B 17/20; A61M 5/00
[52] U.S. Cl. .............................. 604/22; 604/527; 604/264
[58] Field of Search ........................... 604/280, 264, 604/22, 523, 524, 526, 527

[56] References Cited

U.S. PATENT DOCUMENTS

| | | | |
|---|---|---|---|
| 4,951,677 | 8/1990 | Crowley et al. | 128/662 |
| 5,020,539 | 6/1991 | Yokoi et al. | 128/662 |
| 5,348,536 | 9/1994 | Young et al. | 604/43 |
| 5,363,861 | 11/1994 | Edwards et al. | 128/772 |
| 5,388,584 | 2/1995 | King | 128/662.06 |
| 5,460,619 | 10/1995 | Esrock | 604/280 |
| 5,464,398 | 11/1995 | Haindl | 604/280 |
| 5,865,178 | 2/1999 | Yock | 128/660.03 |
| 5,891,088 | 4/1999 | Thompson et al. | 604/95 |

*Primary Examiner*—Corrine McDermott
*Assistant Examiner*—Michael J. Hayes
*Attorney, Agent, or Firm*—Deborah A. Neville

[57] ABSTRACT

A shaft for a probe, especially suited for TEE and nasogastric applications, with superior bite-through resistance in the outermost probe layer. The probe shaft includes a crushproof monocoil surrounded by coiled sheathing and an outermost layer of heat shrinkable polymer tubing. The heatshrinkable polymer provides superior resistance to lacerations from sharp objects such as patients teeth. Moreover, in an embodiment using clear polymer over darker inner layers marked with light colored depth markings, the depth markings are protected from wearing off. The preparation method includes inserting a monocoil and sheath into a tube of heatshrinkable material and applying heat sufficient to cause the heatshrinkable material to mechanically adhere to the sheath.

7 Claims, 2 Drawing Sheets

METHOD AND APPARATUS FOR PREVENTION OF FLUID INTRUSION IN A PROBE SHAFT

FIELD OF USE

This invention relates generally to probes for use within body cavities. More particularly, the invention provides a probe with an improved shaft coating and a method for applying such a coating.

BACKGROUND

Endoscopic technology allows devices to be introduced into the human or animal body and manipulated external to the body. The terms endoscope and endoscopic are used herein to broadly encompass medical or veterinary devices or instruments such as laparoscopes, cytoscopes, colonoscopes, sigmoidoscopes, arthroscopes, esophagoscopes, bronchoscopes, gastroscopes, thoracoscopes, peritoneoscopes, culdoscopes, catheters and the like which are designed to penetrate a body structure, cavity, orifice or lumen and to permit some sort of procedure or therapeutic action. The term "probe" as used herein is intended to include any endoscopic device.

Many of the body cavities and hollow conduits (e.g. peritoneal, abdominal, bronchial, lung, esophagal) can be accessed through endoscopic means without surgical incisions and trauma associated with such incision. Endoscopes typically include a long, thin tubular casing or shaft optically connected to viewing mechanism. The probe shaft is narrow enough to insert through small openings, either natural or surgical, in the body and thereby enter a bodily cavity. As used herein, bodily cavity is intended to include any and all mammalian body cavities, including but not limited to colon, duodenum, esophagus, trachea, bronchii, stomach, lungs, arteries, veins, capillaries, vagina, uterus, gall bladder, ureters, kidneys, peritoneal, and thoracic cavities, synovial spaces, spinal cord cavity, urethra, ducts, and organs such as eye, heart and the like.

Endoscopic technology led to a technique for ultrasonically scanning the heart: transesophageal echocardiography, or TEE. In TEE, an ultrasonic transducer is located at the end of an elongated probe, which is passed through the patient's mouth and into the esophagus or stomach. From such a position within the thoracic cavity, the ribs no longer impede the transmission or reception of ultrasound.

However, in many procedures, the minimization of trauma or discomfort to the patient is paramount. The probe shaft must be smooth on the external surface, facilitating comfortable insertion. The probe shaft must also be flexible, thereby conforming to contours inside the patient's body. Moreover, in a climate of upward spiraling medical related costs, manufacturing, maintenance and repair cost containment is sought for ubiquitous devices such as probes and probe shafts.

Currently used scopes are constructed with a crush proof inner core within which the electrical and mechanical components reside, a sheath element associated with the core to provide torsional stiffness in order that the probe may be rotationally controlled, and some sort of scaled protective coating.

Proper coating of any probe shaft is vital to minimizing trauma and facilitating entrance of the probe into the desired structure or cavity, as well as to protect the probe from body fluids and other fluids capable of damaging the probe elements. The protective coating of the shaft also serves to insulate the patient from contact with electrical components.

The trade off with elastomeric coatings is between flexibility and strength. The more flexible the coating, the more susceptible is the coating to being pierced by a patient's tooth or otherwise abraded or lacerated. Laceration of the protective coating renders a probe shaft virtually unusable, as it can no longer protect the patient from electrical contact with the core, nor can the probe shaft be adequately sterilized.

Current manufacturing methods for covering endoscopic tubing include multiple steps and are limited by the curing time of the primer and polymer coating selected. A commonly practiced method includes selecting a main metallic shaft or core (generally, a steel monocoil—a helically wound metallic strip—covered by a steel braid) and covering the metallic shaft with an extruded thermoplastic tubing suspended in an expanded state in a vacuum. After the metallic shaft has been inserted into the vacuum-expanded extruded tube, the vacuum is removed, and the extruded thermoplastic tubing conforms tightly around shaft. This method, however, requires a primer be applied to the external surface of the steel braid to ensure adhering of the thermoplastic tubing to the metallic shaft.

Another method currently practiced includes priming the surface of the steel braid, followed by application of a thermosetting polymer and curing (cross linking) of the polymer. In this method, thickness uniformity is not easily controlled, and the primer and curing steps both consume valuable manufacturing time.

Further adding to the cost of probe maintenance is the wearing off of depth markings. Depth markings are painted on the exterior of the protective coating and indicate the depth to which the probe has been inserted. The wearing off of depth markings requires the probe be returned for repainting, adding to the need for additional instrument inventory as well as increasing the maintenance cost of the equipment.

SUMMARY OF THE INVENTION

The foregoing and other problems are overcome in accordance with the invention taught herein which relates to a shaft for an invasive bodily probe, particularly a transesophageal or nasogastric probe, which protects the probe from damage through exposure to environmental insults and protects the patient from injury.

The shaft of the invention includes a crush resistant monocoil, a stainless steel braided sheath wrapped thereabout (monocoil and sheath together referred to as the core), and a layer of heat shrinkable material disposed about the braided sheath. It is possible to have more than one layer of heat shrinkable material so disposed. The outermost layer or coating may be transparent and thereby facilitate reading of depth markings upon the inner layer.

The heat shrinkable material typically is adhered to the core along its length by shrinking into the crevices in the surface of the braid. In a preferred embodiment, to prevent the introduction of any bodily fluids, all of the crevices and seams of the braid are filled with the heat shrinkable material so that no gaps exist and no longitudinal movement of fluids between the core and outer layer is permitted. While a sharp object such as a patient's tooth may come into sharp contact with the outer layer, laceration of the outer layer is prevented by the superior cut-through resistance of the heat shrink material.

In a preferred embodiment of the invention, the outer member or tubular coating is typically formed by applying heat to the heat shrinkable material of the outer layer such that the material shrinks around the core and fills the crevices and seams of the braid, forming an elastic casing.

DETAILED DESCRIPTION OF THE PREFERRED EMBODIMENT

Figure 1:
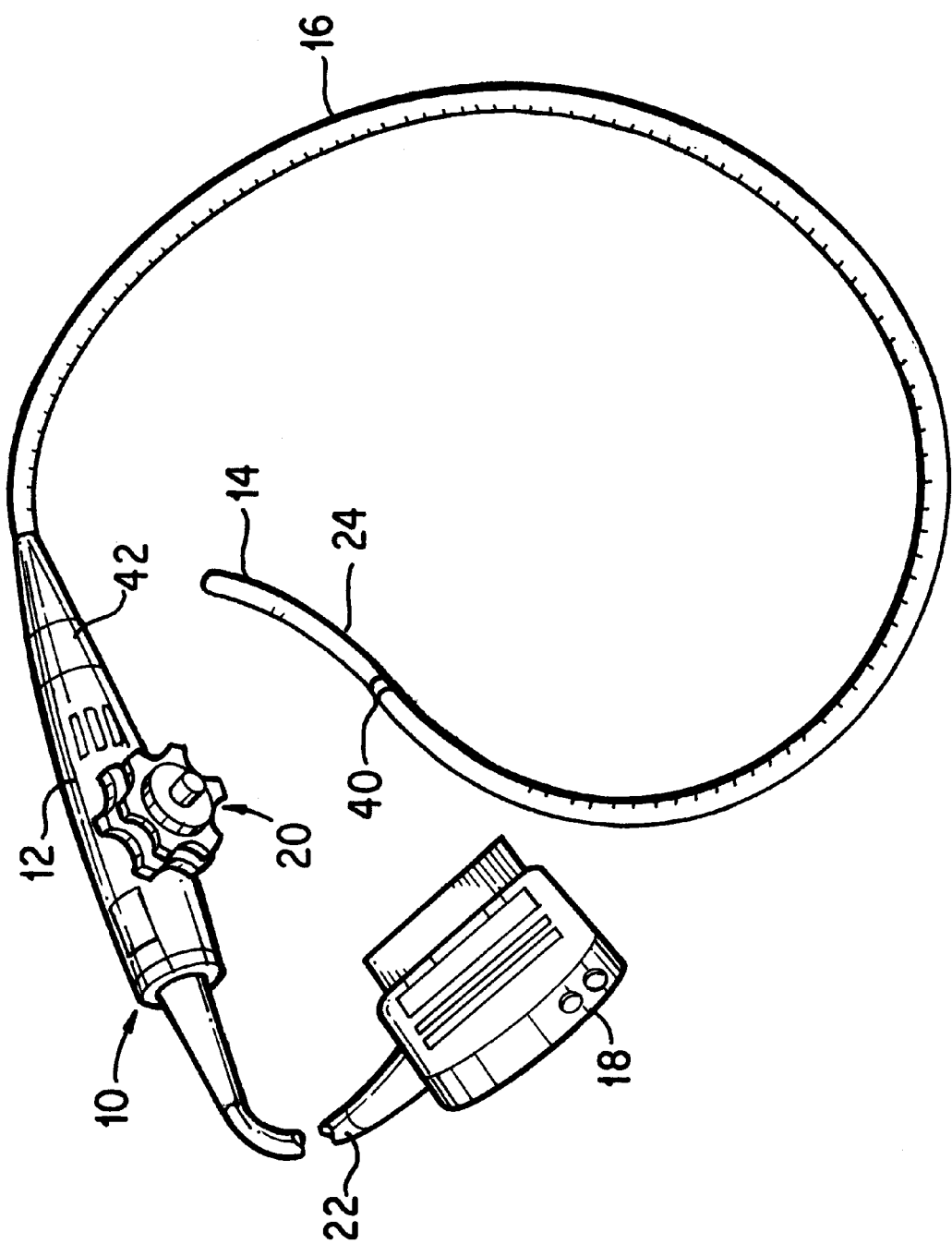
FIG. 1 is a pictorial representation of a transesophageal probe utilizing the shaft of the invention.

Referencing the drawings, FIG. 1 provides a pictorial representation of a typical transesophageal probe 10 with which the shaft of the invention is used. Probe 10 is an ultrasonic probe suitable for insertion into a particular bodily cavity or orifice, namely the esophagus. It is to be understood that this invention is being described with reference to a transesophageal probe for purposes of illustration only, and that this invention has equal applicability to other invasive bodily probes, either medical or veterinary, which utilize a shaft which must be electrically insulated from the body under examination and which is likely to receive environmental insults such as lacerations and immersion in corrosive fluids.

Probe 10 includes a proximal head portion 12, a distal tip portion 14, a somewhat flexible shaft 16 connecting head portion 12 with a distal tip portion 14 and electrical connector 18. Shaft 16 may include a flexible portion 24 adjacent distal tip portion 14 which can be easily articulated using knobs 20. Distal tip portion 14 typically includes a transducer (not shown) and electrical cables 22 travel from connector 18, through head portion 12 and shaft 16 to the transducer. Typically, distal tip portion 14 can be deflected for proper positioning of the transducer by bending of portion 24. This deflection is produced by rotation of wheels 20 which are mechanically coupled to portion 24 by cables and the like (not shown) which travel through shaft 16. The manner of operation of transesophageal probe 10, and the details of its structure are well known to those skilled in the art and need not be set forth.

Typical shafts used comprise three basic components: an inner crush proof monocoil, a stainless steel braided sheath surrounding the monocoil and providing torsional stiffness, and an outer protective elastomeric coating. The probe is inserted through a patient's mouth and down the esophagus for scanning internal organs, including the heart. The smooth elastomeric coating is vulnerable to lacerations from teeth and other sharp surfaces. Once lacerated, repercussions range from difficulty in sterilizing the shaft and damage to electrical components from contact with bodily corrosives, to patient electrical shock from contact with the conductive core.

Shaft 41 of the invention which comprises at least a portion of shaft 16 will now be described with particular reference to FIGS. 1 and 2. Shaft 41 extends between fittings 40 and 42, which assist in securing shaft 41 to adjacent sections of probe 10. Fitting 40 typically is disposed immediately adjacent portion 24, while fitting 42 typically is disposed in head portion 12, although either fitting may be disposed at other positions along shaft 16, the actual location depending on the length of the shaft 16 for which it is necessary that the core be electrically insulated from the patient.

Shaft 41 includes an inner convoluted monocoil 30, a stainless steel sheath 32 surrounding monocoil 30 and a heat shrink outer member 34 covering stainless steel sheath 32. The monocoil 30 is typically composed of stainless steel while the sheath 32 is typically formed of braided stainless steel together referred to as the core. However, it is to be understood that the monocoil 30 may be composed of other materials besides stainless steel, so long as the required strength, rigidity and structural support are provided to prevent crushing of the monocoil. Likewise, the stainless steel braid comprising the sheath 32 may be any material similar in strength, durability and corrosion resistance.

Heat shrink outer member 34 or outer layer will now be described with particular reference to FIG. 2. Member 34 is formed of heat shrink material which is molecularly cross linked thermoplastic polymer. The molecular cross linking which is peculiar to this class of thermoplastic polymers provide great resistance to abrasion and laceration or cut-through. The member provides electrical isolation in the form of a thin yet tough and flexible layer.

Figure 2:
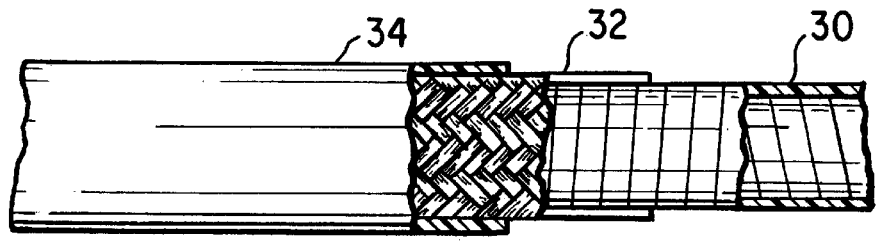
FIG. 2 is a partially cutaway, cross section of the probe shaft of the invention.

In a preferred embodiment as depicted in FIG. 2, the outer layer 34 is composed of thermoplastic polymer that has been irradiated into heat shrink material. Typically a thermoplastic polymer that may be molecularly cross linked as a result of exposure to gamma radiation. The thermoplastics most suitable for practice of the invention include polyvinyl chloride (PVC), polyolefins (polyethylenes), Neoprene (chlorinated rubber) fluoroelastomer (Teflon) and silicones. The outer layer 34 is mechanically attached to the braided sheath 32 for the length of the shaft because the heatshrink material shrinks into the crevices of the braided sheath 32, forming a close physical associated such that liquid cannot insinuate itself between the outer layer 34 and the sheath 32. The result is a thin protective covering for the length of the shaft which is flexible and highly laceration resistant. Typically the shaft thickness is 0.015 to 0.020 inch.

Figure 3:
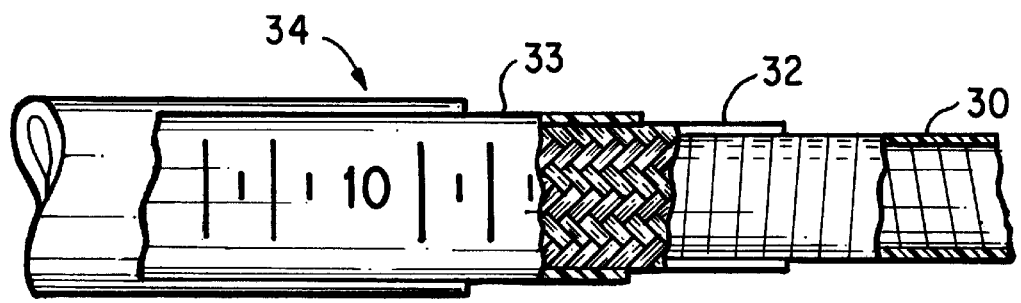
FIG. 3 is a partially cutaway, cross-sectional side view showing the probe shaft of the invention.
Figure 4:
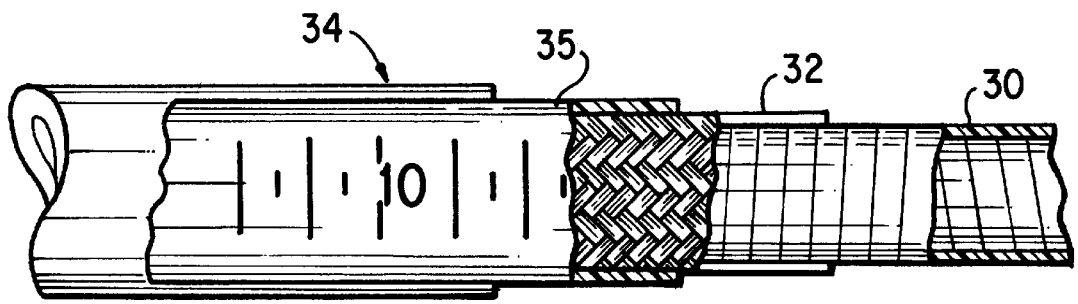
FIG. 4 is a partially cutaway, cross sectional side view showing an embodiment of the invention.

In an alternate embodiment depicted in FIG. 3, the outer layer 34 is composed of a clear thermoplastic polymer beneath which is a layer of urethane 33 or other tough, dark thermosetting polymer and upon which dark urethane layer 33 white depth markings are applied. The urethane layer 33 is in direct contact with the braided sheath 32, having been painted on and cured prior to marking with depth markings and affixing the clear outer layer 34. The depth markings are visible through the clear outer layer, and are, by virtue of the outer layer, protected from wearing off as a result of abrasion or exposure to chemical corrosives or harsh sterilants. Proper depth markings are essential for probes, and re-marking is expensive. The outer layer 34 ensures that the depth marking will not require re-marking as a consequence of depth markings having been worn off. An alternate embodiment is depicted in FIG. 4, and is different from FIG. 3 in the composition of the intermediate layer. Beneath the clear outer layer 34 is a layer of dark heat shrinkable polymer 35 upon which the depth markings have been painted or otherwise affixed. This dark heat shrinkable polymer is thus disposed beneath the clear outer layer 34 and directly upon the braided sheath 32. The selection of the two heat shrinkable polymer layers 34, 35 must take adherence of materials to each other into account. For both embodiments depicted in FIG. 3 and FIG. 4, both layer materials ought to adhere well to each other to create suitable lamination for the length of the shaft.

The method of formation of the shaft will now be described with references to FIG. 2. First, monocoil 30 is formed in a conventional manner by wrapping a strip of stainless steel or the like about a mandrel, as is well known in the art. Thereafter in accordance with conventional assembly techniques, sheath 32 is constructed over monocoil 30 by feeding monocoil through a standard braiding machine. Thereafter, previously irradiated tubular length of thermoplastic polymer is slid over the sheath 32 and monocoil 30. Heat from a convection oven, air blower or other source is applied sufficient that the thermoplastic polymer shrinks, thereby filling the crevices of the braided sheath 32, and leaving no space between the thermoplastic layer 34 and the braided sheath 32 into which liquid may intrude.

The method of formation of the shaft will now be described with references to FIG. 3. First, monocoil 30 is formed in a conventional manner by wrapping a strip of stainless steel or the like about a mandrel, as is well known in the art. Thereafter in accordance with conventional assembly techniques, sheath 32 is constructed over monocoil 30 by feeding monocoil through a standard braiding machine. Black urethane or similar material 33 is painted directly onto the braided sheath 32 and cured. Depth markings are affixed by painting or other means as are well known in the art. Thereafter, previously irradiated tubular length of thermoplastic polymer is slid over the sheath 32 and monocoil 30. Heat from a convection oven, air blower or other source is applied sufficient that the thermoplastic polymer shrinks, thereby filling the crevices of the braided sheath 32, and leaving no space between the thermoplastic layer 34 and the braided sheath 32 into which liquid may intrude.

The method of formation of the shaft will now be described with references to FIG. 4. First, monocoil 30 is formed in a conventional manner by wrapping a strip of stainless steel or the like about a mandrel, as is well known in the art. Thereafter in accordance with conventional assembly techniques, sheath 32 is constructed over monocoil 30 by feeding monocoil through a standard braiding machine. A tubular length of black or dark previously irradiated thermoplastic polymer 35 is slid over the sheath 32 and the monocoil 30. Heat from a convection oven, air blower or other source is applied sufficient that the thermoplastic polymer shrinks, thereby filling the crevices of the braided sheath 32, and leaving no space between the dark polymer layer 35 and the braided sheath 32 into which liquid may intrude. Depth markings are affixed by painting or other means as are well known in the art.

Thereafter, previously irradiated tubular length of clear thermoplastic polymer 34 is slid over the dark polymer 35 layer, sheath 32 and monocoil 30. Heat from a convection oven, air blower or other source is applied sufficient that the thermoplastic polymer shrinks, thereby adhering to the dark polymer layer 35 such that no fluid may be admitted anywhere along the length.

The use of thermoplastic polymer layers seals and insulates the sheath 32 and monocoil 30 all along the length of the sheath 32 and monocoil 30. In the event that the outer layer 34 is bitten into by a patient, it is unlikely that the outer layer 34 will lacerate. Thus electrical connection of the patient to the sheath 32 and monocoil 30 is highly unlikely. Also, gastric juices cannot enter the outer layer 34 because the high resistance to cut through of the outer layer 34. Nor can fluids or bacteria become trapped because the outer layer 34 remains free of cuts. Consequently, the shaft can be fully sterilized.

The use of thermoplastic (heats shrinkable) polymer provides the foregoing advantages, does not increase shaft diameter and, along with increased resistivity to laceration, the polymer allows the shaft to retain a high degree of flexibility. Patient discomfort is minimized and monocoil 30 remains intact enabling proper functioning of necessary electrical and mechanical cables. Also, the application of thermoplastic polymer layers is simple with existing machinery and heat sources.

In view of the foregoing description, it is likely that modifications and improvements which are within the scope of this invention will occur to those skilled in the art. The description herein is intended to be exemplary only, the scope of the inventions being defined by the following claims and their equivalents.

I claim:

1. A shaft for use with a probe adapted to invade a bodily cavity, said shaft comprising:

an inner, electrically conductive core having a length and defining a channel extending along the length of the shaft, said core comprising a monocoil and a braided sheath surrounding said monocoil;

an outer electrically insulating protection coating formed of an irradiated heat shrink material completely surrounding said shaft and mechanically adhering to said braided sheath said coating mechanically adhering due to said coating having contracted after surrounding said braided sheath protection coating comprising a heat-shrink material protecting the depth markings from wearing off, said heatshrink material being sufficiently transparent so that said depth markings may be read, the heatshrink material comprising a two layer electrically insulating member encircling said core wherein a first layer comprises a first heatshrink material, said first material having depth markings, and a second protection layer comprising a second heatshrink material protecting the depth markings from wearing off, said second material being sufficiently transparent so that said depth markings may be read.

2. A shaft as in claim 1 wherein the outer electrically insulative coating is of a material that contracts upon first exposure to temperatures greater than the temperature at which the shaft will operate.

3. A shaft as in claim 2 wherein said electrically insulative coating is formed from a thermoplastic polymer which crosslinks upon irradiation.

4. A shaft as in claim 3 wherein the insulative coating is selected from the group consisting of polyvinyl chloride, polyethylene, chlorinated rubber, fluoroelastomer, and silicone.

5. An ultrasonic probe suitable for insertion into a bodily cavity or orifice, said probe comprising:

a distal tip portion containing a transducer;

a head portion containing means for adjusting the position of said distal tip portion; and a shaft coupling said head portion to the distal tip portion and having a central channel containing electrical and mechanical connections extending from said head portion to said distal portion, said shaft comprising:

a central core enclosing said channel, said core having a length, said core being sufficiently flexible to permit bending of said shaft but being sufficiently rigid to prevent collapse of said channel;

an electrically insulating member formed of an irradiated heat shrink material encircling said core and having a length extending at least along a substantial portion of said length of said core, said member comprising a heat shrinkable, corrosion resistant, flexible tubular coating, said tubular coating being mechanically bonded to said core such that liquid may not intrude between said core and said member;

a two layer electrically insulating member encircling said core wherein a first layer comprises a first heatshrink material, said first material having depth markings, and a second protection layer comprising a second heatshrink material protecting the depth markings from wearing off, said second material being sufficiently transparent so that said depth markings may be read.

6. A probe as in claim 5 further comprising:

a two layer electrically insulating member encircling said core wherein a first layer comprises a first heatshrink material, said first material capable of bearing depth markings, and a second layer comprises a second heatshrink material, said second material sufficiently transparent so that said depth markings may be read.

7. A probe shaft with enhanced lacerative resistance comprising:

an inner, electrically conductive core having a length and defining a channel extending along the length of the shaft, said core comprising a monocoil and a braided sheath surrounding said monocoil;

an outer electrically insulative heat shrinkable and see-through protective coating formed of an irradiated heat shrink material completely surrounding said shaft and an intermediate urethane layer bearing depth markings adhered to said core and beneath said outer coating such that the depth markings are protected from wearing off and are readable.

* * * * *